United States Patent [19]
Richards et al.

[11] 3,975,779
[45] Aug. 24, 1976

[54] ARTIFICIAL INTRAOCULAR LENS AND SUPPORTING SYSTEM THEREFOR

[75] Inventors: William Richards, Medway; Bernard Grolman, Worcester, both of Mass.

[73] Assignee: American Optical Corporation, Southbridge, Mass.

[22] Filed: June 16, 1975

[21] Appl. No.: 587,483

Related U.S. Application Data

[63] Continuation-in-part of Ser. No. 566,542, April 9, 1975, abandoned.

[52] U.S. Cl. ............................................. 3/13
[51] Int. Cl.² ........................ A61F 1/16; A61F 1/24
[58] Field of Search .................... 3/13, 1; 351/160

[56] References Cited
UNITED STATES PATENTS

| | | |
|---|---|---|
| 3,673,616 | 7/1972 | Fedorov et al. ............................ 3/13 |
| 3,866,249 | 2/1975 | Flom ............................................ 3/13 |
| 3,913,148 | 10/1975 | Potthast ..................................... 3/13 |

*Primary Examiner*—Ronald L. Frinks
*Attorney, Agent, or Firm*—H. R. Berkenstock, Jr.; William C. Nealon

[57] ABSTRACT

A lens suitable for implantation in the eye is provided with a supporting system which accommodates to normal function of a dynamic pupil. The supporting system includes flexible spring-like members structurally designed to follow a dilating and contracting pupil while providing longitudinal fixation and centration of the lens.

12 Claims, 11 Drawing Figures

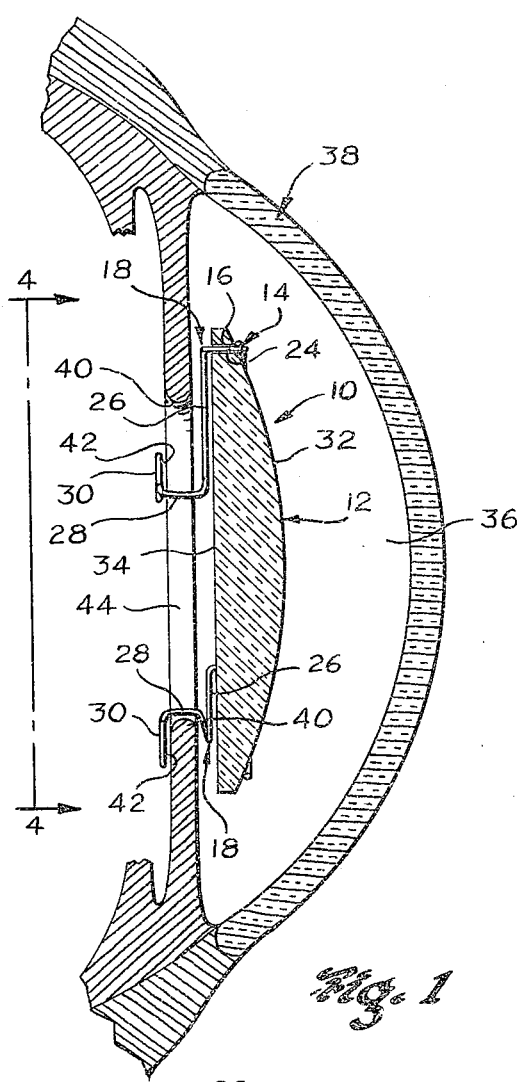
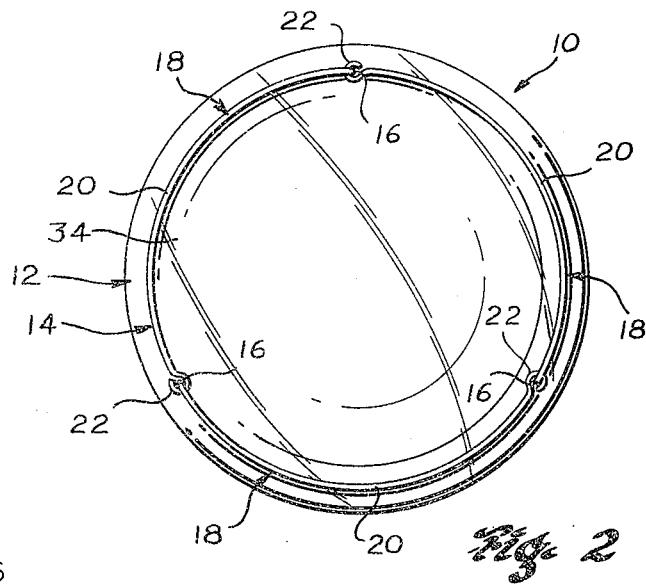
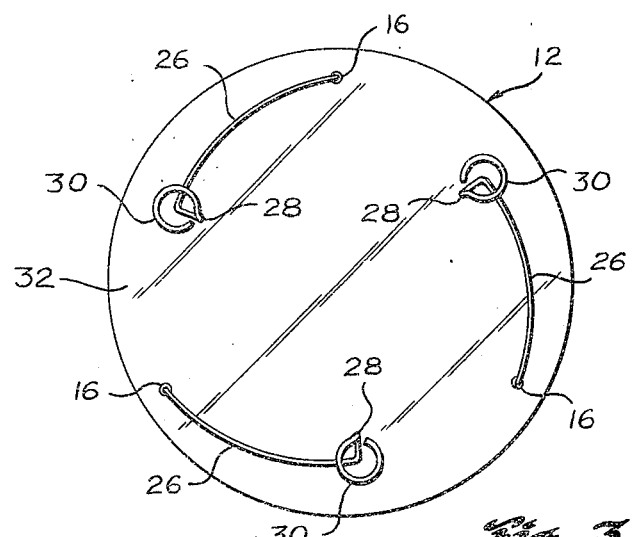
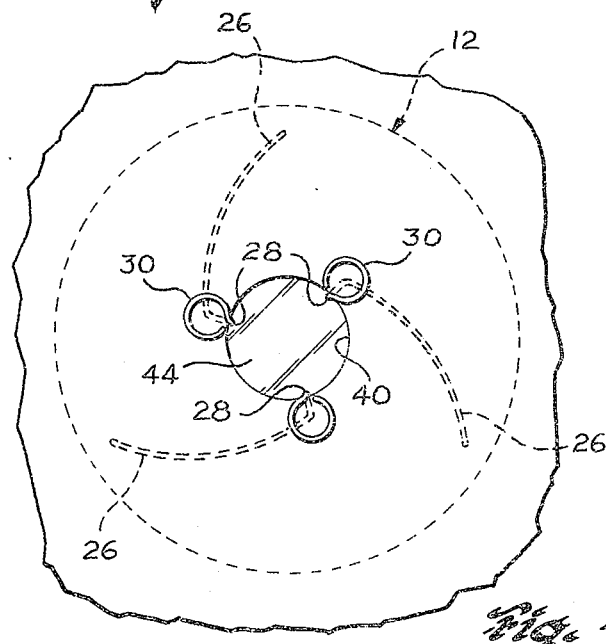
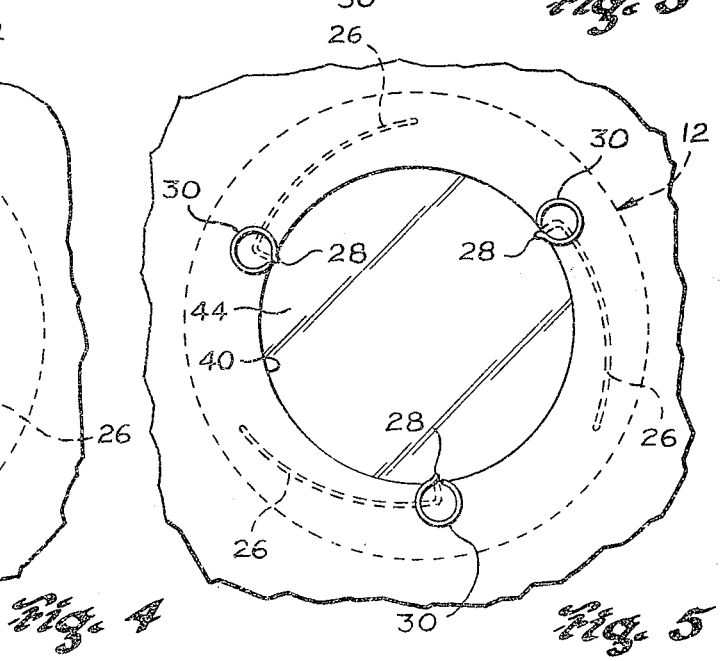

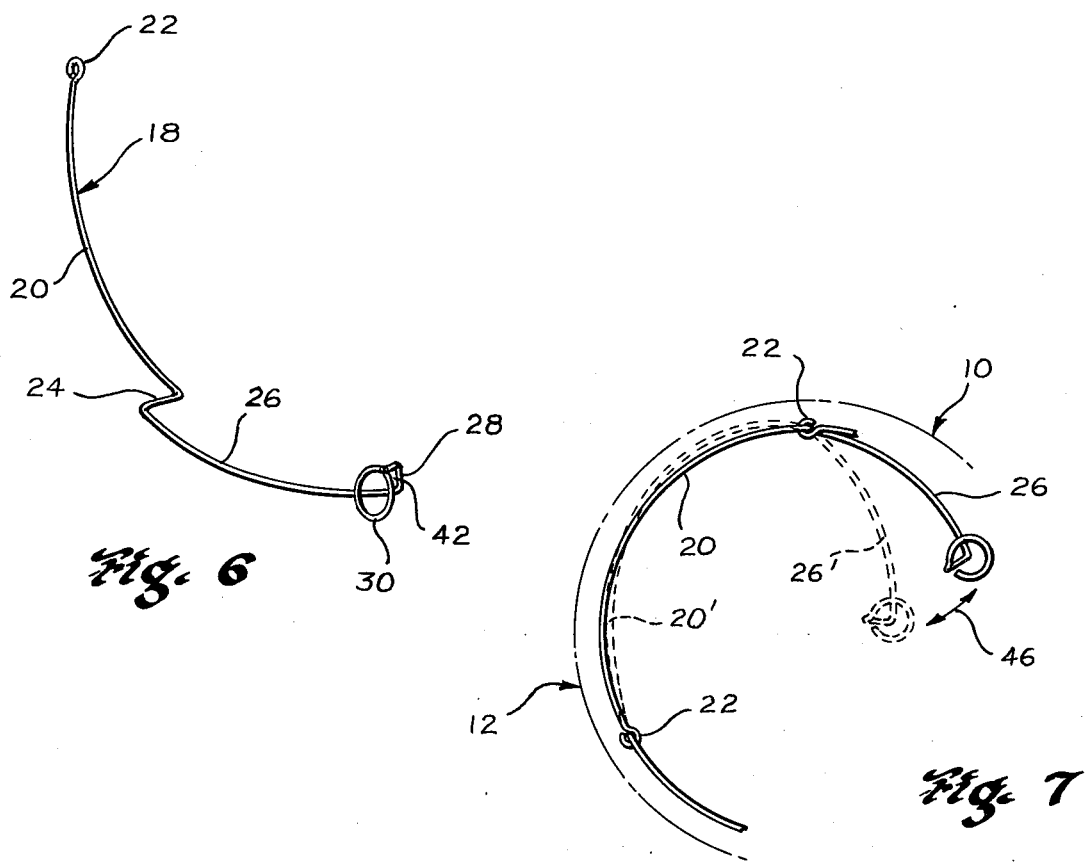

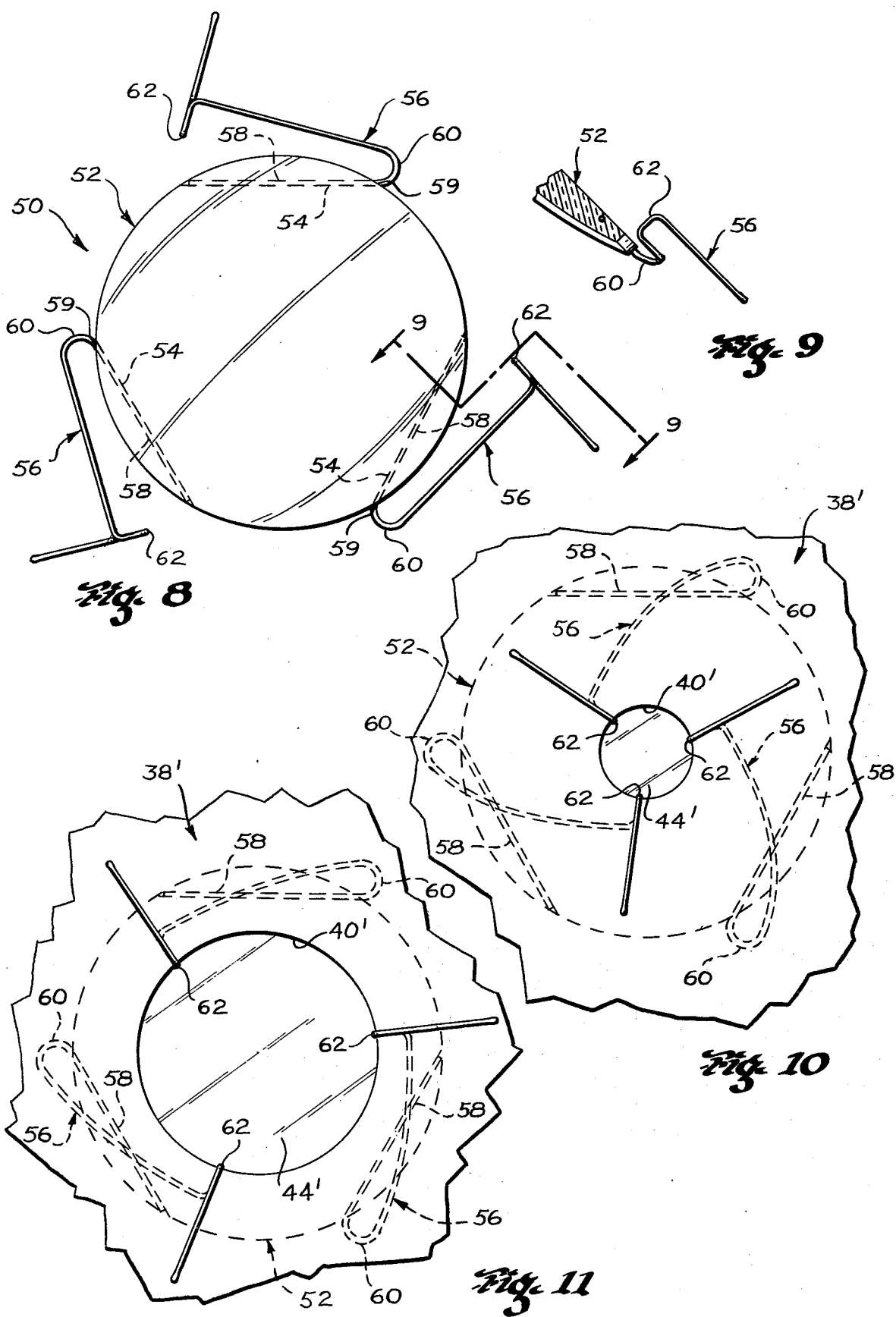

ARTIFICIAL INTRAOCULAR LENS AND SUPPORTING SYSTEM THEREFOR

This is a continuation-in-part of application Ser. No. 566,542 filed Apr. 9, 1975, now abandoned.

BACKGROUND OF THE INVENTION

Field of the Invention

This invention relates to improvements in ophthalmology and more particularly to supporting systems for artificial intraocular lenses (pseudophakoi) used for the correction of aphakia and re-establishment of binocularity in aphakia.

Discussion of the Prior Art

Well-fixed and well-centered intraocular lens implants are known to produce stable retinal images and offer the best chance of re-establishment of binocularity in cases of aphakia. However, a characteristic common to presently employed lenses, which thwarts the normal activity of the aphakic eye's pupil, is the maintenance of a constant minimal pupil size. That size is determined by the radial spacing of the posterior projections of the post-irido loops or clips. A pilocarpine regimen is usually employed to sustain this minimum size in an effort to preclude accidental lens dislocation occurring as a result of pupil dilation.

Accordingly, a lens support or fixation design which did not interfere with normal pupil function would represent an exceptional advance in the art and it is a principal object of the present invention to provide such a lens support, i.e. to provide a lens fixation design wherewith ordinary pupil function can continue following implantation of a pseudophakos and danger of its dislocation by reaction to ambient illumination or medically induced dilation for eye examination purposes can be obviated.

SUMMARY OF THE INVENTION

The aforesaid objective and its corollaries are accomplished by the provision of an anterior chamber implant lens whose iridocapsular support consists of several flexible spring-like members structurally designed to follow or accommodate to the dynamic pupil as well as providing longitudinal fixation and centration.

Each of the pupil follower members is fixed to the lens adjacent its periphery and terminates in a U-shaped configuration forming a clip into which the irido-pupillary margin may be fitted.

The presently contemplated iris follower system insures that as the pupil diameter changes, the point of contact of each U-shaped clip with the pupil margin remains fixed, i.e. substantially no sliding action occurs along the pupil margin, and the possibility of lens dislocation occurring as a result of pupil dilation is eliminated.

Details of the invention will become more readily apparent from the following description when taken in conjunction with the accompanying drawings.

IN THE DRAWINGS

FIG. 1 is an illustration, in side elevation, of a preferred embodiment of a pseudophakos in situ, the eye being shown in cross-section for clarity of illustration;

FIG. 2 is a front elevational view of the pseudophakos;

FIG. 3 is a rear elevational view of the same pseudophakos;

FIG. 4 is a fragmentary rear elevational view of the iris of the eye of FIG. 1 taken generally from the position of line 4—4 and illustrating a condition where the iris, with the pseudophakos attached, is contracted to nearly a minimum pupil diameter;

FIG. 5 is a view similar to FIG. 4 but illustrating a nearly maximum pupil dilation;

FIG. 6 is a view, in perspective, of one element of the three element lens supporting system shown in FIGS. 1-3; and FIG. 7 is a skeletonized fragmentary front elevational view of the same pseudophakos, its lens being shown with phantom outline for convenience and clarity in illustrating functional characteristics of the supporting system.

FIG. 8 is a front elevational view of a modification of the invention;

FIG. 9 is a fragmentary cross-sectional view taken along line 9—9 of FIG. 8;

FIG. 10 is a fragmentary rear elevational view of the iris of an eye which is illustrated in a condition where the iris, with the pseudophakos of FIG. 8 attached, is contracted to nearly a minimum pupil diameter; and FIG. 11 is a view similar to FIG. 10 but illustrating a nearly maximum pupil dilation.

DESCRIPTION OF THE PREFERRED EMBODIMENTS

Referring more particularly to FIGS. 1-5, pseudophakos 10 comprises an optical section (lens 12) and a fastening or haptic section (lens supporting system 14).

Lens 12 is formed of a material which is biologically inert, i.e. not susceptible to being absorbed by body fluids and capable of being well tolerated by the human body when implanted. Exemplary materials are quartz, ophthalmic glass, methylmethacrylate resins such as those available under the tradenames "Lucite" and "Plexiglass" and biologically neutral, chemically pure polymethylmethacrylates or biologically inert polymeric materials.

Supporting system 14 is, for similar reasons of avoiding irritation and/or human body rejection of its components, formed of a biologically inert material such as platinum, titanium or an extruded polyamide such as nylon. The supporting system 14 will be described hereinafter as being formed of "wire", it being understood that the term "wire" as used in this specification and its appended claims is intended to include strands, strips or rods of biologically inert material whether such material is metallic or plastic and/or whether one or the other is used exclusively throughout system 14 or the system is made up of both.

The two main sections of pseudophakos 10, namely lens 12 and supporting system 14, are shown in FIGS. 1-5 and 7 as being in operatively assembled relationship with each other and one of three identical components 18 of the supporting system is singularly depicted in FIG. 6 for clearer illustration of its structural details.

Lens 12 is provided with three equally radially and circumferentially spaced openings 16 through each of which, one of the three identically formed wire components 18 of system 14 is extended. It is to be understood that more or less openings in lens 12 and corresponding numbers of components 18 may be used within the general notion of the present invention.

Referring more particularly to FIG. 6, it can be seen that each component 18 comprises a relatively long arcuate extension 20 which, as best shown in FIG. 2, is of such precontrolled length and curvature as to reach from one opening 16 in lens 12 to the next along an arcuate path approximately following the contour of the edge of lens 12. Extension 20 is terminated with an integrally formed hook 22.

Oppositely of its hook 22, the wire of each component 18 is provided with an approximately right-angular bight 24 which, as can be seen in FIG. 1, is extended through one of openings 16 in lens 12. Beyond bight 24, arm 26 is provided with a second approximately 180° bight 28 from which the direction of the wire making up component 18 is reversed and thence formed into the configuration of a loop 30. Loop 30 constitutes a posterior iris clip of the pseudophakos 10.

In FIGS. 1–3, it is shown that lens supporting system 14 comprises three wire components 18 each having its bight 24 extended through one of openings 16 in lens 12. Thereby, corresponding extensions 20 and arms 26 rest against the anterior and posterior surfaces 32 and 34 respectively of lens 12. The lens is thus longitudinally fixed and centered in system 14, it being completely captured by a union of the three anterior extensions 20 which are interlocked by hooks 22 as best illustrated in FIG. 2.

In use, pseudophakos 10 is positioned within the anterior chamber 36 of an eye (FIGS. 1, 4 and 5). The irido-pupillary margin 40 of eye 38 is fitted into a channel 42 formed between loop 30 and spring arm 26 adjacent the bight 28 of each of all three wire components 18. When so in place, pseudophakos 10 is fixed against longitudinal displacement in the eye and is centered over pupil 44 permitting normal pupil function, i.e. dilation and contraction in response to ambient illumination and/or convergence-related posture. Components 18 of supporting system 14 being highly flexible produce only a gentle holding force against the irido-pupillary margin and remain fixed against sliding action along the pupil margin at all times during normal pupil function.

FIGS. 4 and 5 diagrammatically represent approximate extremes of contraction and dilation respectively of pupil 44, both occurring without sliding action of loops 30 along the pupil margin and further without release of loops 30 at any point between such extremes of contraction and dilation.

In order to more clearly illustrate the operation of lens supporting system 14 in its function of following pupil diameter changes without sliding action along the pupil margin and with minimal substantially uniform force of contact against the pupil at all times, i.e. during all stages of dilation and contraction thereof, the skeletonized front elevational view of pseudophakos 10 in FIG. 6 is referred to.

In FIG. 7, it can be seen that both the extension 20 and arm 26 of a component 18 are caused to flex when, for example, arm 26 is moved in the direction of arrow 46, e.g. as a result of pupil contraction to the extent illustrated by dot-dash outline 20' and 26'. Dilation of a pupil accordingly causes reverse flexing of extension 20 and arm 26, e.g. from positions 20', 26' back to the full line illustration of these components.

The effective lever arm of flexibility of each component 18, i.e. in response to pupil contraction and dilation, comprises the combined lengths of arm 26 and extension 20. This cooperative flexing feature of arm 26 and extension 20 is effected by an interconnecting tortional movement of bight 24 in its extension through lens 12.

Exemplary and useful, but not necessarily restrictive, dimensional parameters for pseudophakos 10 are:
Optical section (lens 12)
1. diameter = 4 to 5 mm
2. equivalent power in aqueous = approximately 20 diopters Haptic section (lens supporting system 14)
1. diameters of wire components 18 = approximately 0.1 to 0.5 mm
2. clearance between loops 30 and spring arms 26 (iris receiving channel 42) = from approximately 0.5 to 0.7 mm, i.e. enough to allow the iris diaphragm to fit relatively freely but not loosely therebetween.

The embodiment of the invention described hereinabove for purposes of illustration is not to be interpreted as restrictive of the invention beyond that necessitated by the following claims. Those skilled in the art will readily appreciate that various modifications and adaptations of the precise form here shown may be made to suit particular requirements. It is, accordingly, intended that such modifications which incorporate the novel concept disclosed are to be construed as coming within the scope of the claims or the range of equivalency to which they are entitled in view of the prior art.

Exemplary of a modification of the invention is pseudophakos 50 shown in FIGS. 8–11.

Respecting this embodiment of the invention, the optical section of pseudophakos 50 comprises lens 52 which is formed of a biologically inert material, examples of which have been given hereinabove in connection with the description of lens 12.

Lens 52, however, is provided with a plurality (e.g. three) of approximately equally circumferentially spaced chordal openings 54 which support the haptic section of pseudophakos 50.

The haptic section in this case comprises a plurality of lens-supporting spring arms 56 having their respective proximal sections 58 extended one into each of openings 54 and secured thereinplace. Sections 58 of arms 56 may be press fitted or cemented in openings 54. It is also contemplated that the termini of sections 58 may be slightly beaded or otherwise headed (e.g. with applied heat or high frequency hammering) to prevent withdrawal and/or turning of arms 56.

Adjacent to points 59, where sections 58 emerge from openings 54, the arms 56 are provided with bends 60 which direct them somewhat rearwardly of lens 52 and generally reversely of their respective sections 58. A preferred extent and direction of bending, with arms 56 relaxed (i.e. not under bending tension), is illustrated in FIGS. 8 and 9.

Terminally, arms 56 are provided with bights 62 each of which form a posterior iris clip.

In use, pseudophakos 50 is positioned within the anterior chamber of an eye and each of bights 62 are fitted over the irido-pupillary margin of the eye. The irido-pupillary margin 40' of an exemplary eye 38' is shown in FIGS. 10 and 11. This requires arms 56 to be sprung toward the center of lens 52 to the approximate extent shown in FIGS. 10–11. Lens 52 thus rests forwardly of the iris and becomes substantially centered with pupil 44'.

Bights 62 protect against longitudinal displacement of the pseudophakos in the eye while pupil function (dilation and contraction) is permitted. Arms 56, being highly flexible, produce only a gentle holding force against the irido-pupillary margin and follow its normal dilation and contraction which is substantially, if not completely, uninhibited by pseudophakos 50.

FIGS. 10 and 11 diagrammatically illustrate approximate extremes of contraction and dilation respectively of pupil 44.

It is to be understood that while various materials may be used for the construction of arms 56, biologically inert materials such as platinum, titanium or an extruded polyamide such as nylon have been found to produce desirable results. Exemplary and useful dimensional parameters for lens 52 of pseudophakos 50 are the same as those given hereinabove for lens 12 of pseudophakos 10.

The diameter of each arm 56 may be from approximately 0.1 to 0.5mm with a clearance within bight 62 in each case which is sufficient to freely but not loosely receive the iris diaphragm. A spacing of from approximately 0.5 to 0.7 mm has been found to produce desirable results.

We claim:

1. A pseudophakos comprising:
a lens;
a plurality of slender and resilient supporting arms affixed to said lens adjacent its periphery and each extending along one side thereof;
each of said arms terminating with an iris clip portion for receiving the irido-pupillary margin when the pseudophakos is implanted for use;
said arms being lightly spring biased toward the periphery of said lens and so proportioned as to resiliently urge their corresponding clip portions against said pupillary margin with a gentle holding force when the pupil is approximately maximally dilated and to follow said pupillary margin to the extent of maximum pupillary contraction substantially without affect upon normal pupil function whereby dislocation of the implanted pseudophakos occurring as a result of dilation and contraction of a dynamic pupil is prevented.

2. A pseudophakos according to claim 1 wherein said lens has a plurality of openings adjacent its periphery and said supporting arms are disposed posteriorly of said lens, each arm including a bight extending through one of said openings and a forward extension disposed anteriorly of said lens, said extensions being successively interconnected whereby said holding force against said pupillary margin is cushioned by the combined resiliencies of said arms and their respective extensions.

3. A pseudophakos according to claim 2 wherein said openings in said lens are three in number and are substantially equally radially and circumferentially spaced thereabout, said supporting arms and corresponding forward extensions thereof respectively also being three in number.

4. A pseudophakos according to claim 1 wherein said slender and resilient supporting arms are formed of a substantially clear plastic material.

5. A pseudophakos according to claim 1 wherein said slender and resilient supporting arms are formed of metal.

6. An irido-capsular supporting system for an artificial intraocular lens comprising:
an annular array of a plurality of wire components;
each component having an anterior section, an intermediate bight and a posterior lens supporting arm terminating with an iris clip portion, said bight of each component being adapted to extend through a peripherally disposed opening in a lens intended to receive said supporting system whereby, said lens may be captured between said anterior sections and arms, the later being adapted to receive the irido-pupillary margin within respective clip portions thereof.

7. An irido-capsular support according to claim 6 wherein said array of wire components is comprised of three such components.

8. An irido-capsular support according to claim 6 wherein said wire components are formed of a substantially clear plastic material.

9. An irido-capsular support according to claim 6 wherein said wire components are formed of metal.

10. An irido-capsular supporting system according to claim 6 wherein said anterior sections of said wire components are arcuately shaped and each terminate with a hook portion, said hook portion of one of said components being adapted to engage the bight of an adjacent component in said annular array thereof when said supporting system is applied to said lens.

11. A pseudophakos according to claim 1 wherein said lens has a plurality of chordal openings adjacent its periphery with said supporting arms proximally fixed therewithin.

12. A pseudophakos according to claim 11 wherein said arms are permanently bent adjacent their respective chordal openings each in a direction generally reversely of and toward parallelism with its extension in a chordal opening when said arm is in a relaxed condition.

* * * * *